(12) United States Patent
Florman

(10) Patent No.: US 8,439,676 B2
(45) Date of Patent: May 14, 2013

(54) PERIODONTAL INTERDENTAL DELIVERY TRAY AND PERIODONTAL MEDICAMENT TRAY SYRINGE

(76) Inventor: Michael Florman, Los Angeles, CA (US)

(*) Notice: Subject to any disclaimer, the term of this patent is extended or adjusted under 35 U.S.C. 154(b) by 45 days.

(21) Appl. No.: 12/842,697

(22) Filed: Jul. 23, 2010

(65) Prior Publication Data

US 2011/0065061 A1  Mar. 17, 2011

Related U.S. Application Data

(60) Provisional application No. 61/228,124, filed on Jul. 23, 2009, provisional application No. 61/228,287, filed on Jul. 24, 2009.

(51) Int. Cl.
*A61C 17/00* (2006.01)

(52) U.S. Cl.
USPC .................................................. 433/80

(58) Field of Classification Search .......... 433/80, 433/81, 82, 215, 89, 216–217.1, 214, 6, 24; 601/162–165; 128/859–862; 424/49–53; 514/900–902
See application file for complete search history.

(56) References Cited

U.S. PATENT DOCUMENTS

| | | | |
|---|---|---|---|
| 3,874,084 A | 4/1975 | Cole | |
| 4,138,814 A | 2/1979 | Weitzman | |
| 4,428,373 A | 1/1984 | Seid et al. | |
| 4,902,227 A | 2/1990 | Smith | |
| 5,085,585 A * | 2/1992 | Zimble | 433/80 |
| 5,330,357 A | 7/1994 | Keller | |
| 6,966,773 B2 | 11/2005 | Keller | |
| 2008/0050693 A1 * | 2/2008 | Fischer et al. | 433/25 |

* cited by examiner

*Primary Examiner* — Yogesh Patel

(57) ABSTRACT

The present invention relates to a periodontal interdental tray and to a periodontal medicament tray syringe that can be used in conjunction with the periodontal interdental tray of the present invention, or can be utilized by itself or in conjunction with other periodontal trays already on the market. In one embodiment, the present invention relates to treatment of periodontal disease, and in particular to a dental tray syringe and method for delivering medicaments into areas of the mouth either supragingival or subgingivally to treat the infected areas.

8 Claims, 16 Drawing Sheets

PERIODONTAL INTERDENTAL DELIVERY TRAY AND PERIODONTAL MEDICAMENT TRAY SYRINGE

RELATED APPLICATION DATA

This patent application claims priority to U.S. Provisional Patent Application No. 61/228,124, filed on Jul. 23, 2009, entitled "Periodontal Interdental Tray;" and U.S. Provisional Patent Application No. 61/228,287, filed Jul. 24, 2009, entitled "Periodontal Tray Syringe," the entireties of which are hereby incorporated by reference herein.

FIELD OF THE INVENTION

The present invention relates to a periodontal interdental tray and to a periodontal medicament tray syringe that can be used in conjunction with the periodontal interdental tray of the present invention, or can be utilized by itself or in conjunction with other periodontal trays already on the market. In one embodiment, the present invention relates to treatment of periodontal disease, and in particular to a dental tray syringe and method for delivering medicaments into areas of the mouth either supragingival or subgingivally to treat the infected areas.

BACKGROUND OF THE INVENTION

Periodontal (gum) disease affects a majority of adults at some time in their lives, usually having no warning signs until advance stages of the disease state exist. Treatment methods depend upon the type of disease and how far the condition has progressed. When periodontal pockets become greater than 3 mm between teeth and gums, it is difficult or impossible for the patient to thoroughly remove plaque and tartar. While professional dental cleanings can clean periodontal pockets that exist in the range less than 5 mm, surgery may be necessary to reduce the depth of the pockets or to restore or reshape bone that has been destroyed and create an architecture that is conducive to cleaning. In an attempt to avoid such invasive dental or dental surgical procedures, treating the affected areas with antibacterial or antimicrobial agents (i.e., chemical, antibiotic, or other pharmacological agents) to restore periodontal health have been developed and are being performed. Such antibacterial or antimicrobial agents have been found to control or stop the growth of bacteria that create toxins and cause periodontal disease and encourage normal healing, thereby reducing the necessity or the invasiveness of periodontal or oral surgery. Problems arise that the frequency of administration of these drugs is not practical, seeing they need to be done in the dental chair by a trained dentist or dental hygienist. Other means of cleaning these periodontal pockets include manual brushing of the periodontal pocket using small brushes or interdental brushes. Problems with current interdental brushes is that the patient has a very difficult time finding the periodontal defects, and even when found, access is not easy, due to their location, position, or depth. When multiple sites exist in various locations, the task becomes impossible to perform with accuracy and enough frequency.

Several methods have been developed for treating periodontal disease that enable medicament to be delivered to the infected site below the gingiva. For example, U.S. Pat. No. 5,085,585 discloses an applicator of dental medicament and method of use.

Additionally, as set forth in U.S. Pat. No. 5,330,357 describes medicaments that can be delivered in close proximity to the bone and supporting structure of the teeth by flossing using tufted floss, brushing using an interdental brush, injection using a syringe, or by hydrostatic or mastication pressure using a dental tray. Dental trays often are constructed from a soft plastic elastomeric material that is molded in place to a patient's teeth so as to firmly and closely fit in place on the patient's teeth, and a seal is made to hold the tray solidly against the dental tissues. Medicament is placed in recesses formed in the tray that are adapted to accommodate the patient's teeth, and then guided or forced along the teeth and into the gingiva by the sealing means to the infected site as the patient closes his jaw on the tray. A propulsion agent such as hydrogen peroxide also can be placed in the recesses to guide or force the medicament into the infected site as the hydrogen peroxide breaks down and increases the pressure within the recesses.

Other examples of dental trays are set forth in U.S. Pat. Nos. 4,902,227; 4,428,373; and 4,138,814. While these types of dental trays do allow for application of the medicament subgingivally, none of these references connect the periodontal pocket to a cannuli leading outside of the mouth.

U.S. Pat. No. 3,874,084 discloses a molded tooth cleansing and gingival therapeutic device that includes a plurality of bristles projecting inwardly from the inner walls of the upper and lower channels of a tray. The bristles are provided to clean food particles and bacteria from the surfaces of a user's teeth and the gingival crevices. The walls of the channels are of a sufficient thickness to form ridges or ledges extending away from the gingival lines. These ridges compress the gingiva to allow for cleansing of the gingival crevice between the teeth and gum and massaging of the free marginal gingival.

U.S. Pat. No. 6,966,773 discloses dental tray and method for treatment of periodontal disease that provides a seal around teeth associated with the infected area to guide or force medication onto the surface of the teeth and subgingivally into the infected area and a propulsive agent such as peroxide.

What all these systems do have failed to achieve is a true micro syringe that can be loaded like a similar syringe, and use force from a plunger to inject medicaments into multiple periodontal sites. One of the major failures of inventors of trays in the past is that their trays do not truly inject medicaments and rely on weak physical properties that do not allow medicaments to enter diseased pockets. Some systems of the prior art even rely on claims of propellants used to push medicaments into periodontal sites, relying exclusively on oxygen releasing compounds such as peroxide, which may not be desired to be mixed with other therapeutics such as antibiotics such as Arestin, or Atridox. Companies that sell drugs such as Arestin, or Atridox approved by the FDA for in-office administration have achieved little success due to the fact that these drugs were designed for in-office delivery with weeks between dosings. For example, systemic antibiotic dosing is 4 times per day for 10 days by the patients at home. This is impractical due to the patient's inability to go to the dentist for 40 visits over a 10 day period. Such a tray system and method of treatment easily and conveniently allows therapeutics to be administered by the patient, without special training or undue skill, and not need to be worn for extended periods of time at each application.

Given the above, there is a need in the art for an improved periodontal interdental tray and/or a syringe that permits the more effective treatment of periodontal conditions.

SUMMARY OF THE INVENTION

The present invention relates to a periodontal interdental tray and to a periodontal medicament tray syringe that can be used in conjunction with the periodontal interdental tray of the present invention, or can be utilized by itself or in conjunction with other periodontal trays already on the market. In one embodiment, the present invention relates to treatment of periodontal disease, and in particular to a dental tray syringe and method for delivering medicaments into areas of the mouth either supragingival or subgingivally to treat the infected areas.

In one embodiment, the invention described here allows for repeatable delivery of medicaments into a periodontal pocket through the creation of a true syringe when using the invention with a plunger pushed through a tube into the periodontal pocket. In another embodiment, the present invention also permits for repeatable curettage using fine instruments pushed through the tubes into the periodontal pocket. In still another embodiment, the present invention permits for the repeatable lavage, by using the tube to connect a source of medicated or non-medicated liquids energized, or not, directed into the periodontal pocket.

In another embodiment, the present invention relates to a periodontal tray system comprising: a first inner tray layer that is designed to conform to at least a portion of an individual's mouth, wherein the first inner tray layer is designed to have one or more indentations, or pockets, formed therein that correspond to at least one area of periodontal disease; and a second outer tray layer that is designed to operatively engage the first inner tray layer, wherein the one or more indentations, or pockets, formed in the first inner tray layer contain one or more medicaments, or compounds, designed to treat one or more aspects of periodontal disease, and wherein the second outer tray layer is designed to operatively engage the first inner tray layer so as to permit the delivery of the one or more medicaments, or compounds, contained in the one or more indentations, or pockets, formed in the first inner tray layer into the at least one area of periodontal disease.

In still another embodiment, the present invention relates to a periodontal tray system comprising: a first tray layer that is designed to conform to at least a portion of an individual's mouth, wherein the first inner tray layer is designed to have one or more openings therein that correspond to at least one area of periodontal disease, wherein the one or more openings formed in the first tray layer are designed to operatively couple one or more syringes, or micro-syringes, and wherein the one or more syringes, or micro-syringes, contain one or more medicaments, or compounds, designed to treat one or more aspects of periodontal disease.

In still another embodiment, the present invention relates to a periodontal tray system comprising: a first tray layer that is designed to conform to at least a portion of an individual's mouth; and one or more openings formed in the first tray layer, wherein the one or more openings correspond to at least one area of periodontal disease, wherein one or more openings formed in the first tray layer are designed to operatively couple with one or more devices designed to provide one or more medicaments, or compounds, designed to treat one or more aspects of periodontal disease.

In still another embodiment, the present invention relates to a method to fabricate the periodontal tray system, the method comprising the steps of: (i) placing one or more small barbed broaches into one or more periodontal pockets, wherein the one or more small barbed broaches are designed to function in conjunction with a dental molding material, or impression material, that is used to duplicate various teeth and mouth structures; (ii) creating a mold of one or more areas surrounding the one or more periodontal pockets, wherein the mold contains one or more openings formed therein that correspond to the placement of the one or more small barbed broaches; and (iii) using the mold of Step (ii) as either a periodontal tray, or as an impression to produce a periodontal tray, wherein the periodontal tray contains one or more openings therein that correspond to one or more periodontal pockets, wherein the one or more openings are designed to connect to one or more treatment devices (e.g., a tube/syringe combination, or a syringe).

DETAILED DESCRIPTION OF THE INVENTION

Figure 1:
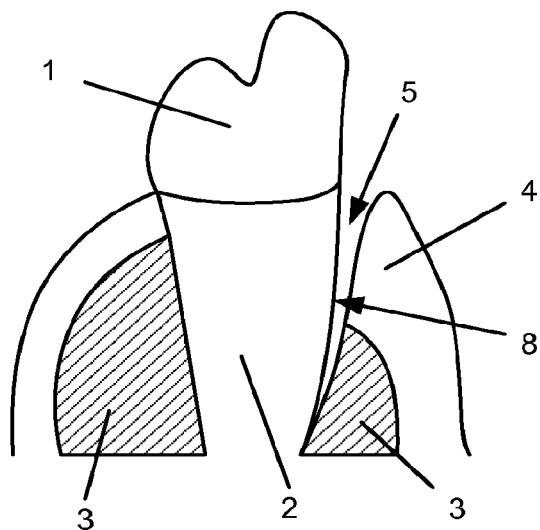
FIG. 1 is an illustration of a tooth.

The present invention relates to a periodontal interdental tray and to a periodontal medicament tray syringe that can be used in conjunction with the periodontal interdental tray of the present invention, or can be utilized by itself or in conjunction with other periodontal trays already on the market. In one embodiment, the present invention relates to treatment of periodontal disease, and in particular to a dental tray syringe and method for delivering medicaments into areas of the mouth either supragingival or subgingivally to treat the infected areas.

In one embodiment, the invention described here allows for repeatable delivery of medicaments into a periodontal pocket through the creation of a true syringe when using the invention with a plunger pushed through a tube into the periodontal pocket. In another embodiment, the present invention also permits for repeatable curettage using fine instruments pushed through the tubes into the periodontal pocket. In still another embodiment, the present invention permits for the repeatable lavage, by using the tube to connect a source of medicated or non-medicated liquids, energized or not, directed into the periodontal pocket.

In another embodiment, the present invention is a periodontal interdental delivery tray system fitted to one or more teeth of a patient's upper and/or lower dental arch provided for the application of medications to the teeth or gum tissue, bone or periodontal ligament for treatment of periodontal disease. The tray system described can guide cleaning brushes or other interdental periodontal aids into one or more periodontal pockets. The tray system can also direct streams of liquids, medicated or not, into the periodontal pockets. The trays are constructed from a variety of resilient materials molded to conform to the teeth, gum tissues, and jaws. The interdental tray system includes at least one layer of material, but can include multiple layers, molded into trays that are compressible and resilient thereby permitting the one or more trays of the present invention to return to their original shape(s) after deformation.

In one embodiment, the overall tray system of the present invention comprises a first tray layer that is formed from an impression of a patient's mouth, or a portion thereof, where the impression permits the tray system to contain one or more impressions that correspond to the one or more periodontal pockets that may exist in a patient's mouth. In one embodiment, the present invention permits a fitting to be affixed to each impression (or hole). The fitting can be designed to either receive a liquid, periodontal aid, or liquid stream.

In another embodiment, the one or more fittings can connect to one or a series of tubes or cannuli. These tubes can be connected to an additional fitting that can either be alone or arranged in a row. Through each opening of the fitting connected to the tube connected to the fitting affixed to the tray, a liquid or micro brush, or pressurized liquid spray, or sonically energized liquid stream, medicated or not, can be pushed, injected or supplied to a desired area for the purposes of effecting a treatment. Methods for fabricating the trays in the tray interdental system, loading the trays with medicaments, delivering the medicaments into the periodontal pocket or defect, pushing liquids through the tray, and or inserting micro periodontal aids into the periodontal pockets will be described below.

A tray syringe system fitted to one or more teeth of a patient's upper or lower dental arch provided for the application of medications to the teeth or gum tissue, bone or periodontal ligament for treatment of periodontal disease. The trays are constructed from a variety of resilient materials molded to conform to the teeth, gum tissues, and jawbones. The tray syringe system includes at least one layer of material, but can include multiple layers, molded into trays that are compressible and returns to its shape after deformation. The first tray layer when formed acts as a receptacle for medicaments. The receptacle or receptacles are fabricated in positions specifically desired by the dentist or physician corresponding to where the periodontal disease site is, either on the tooth, gums, or bone surrounding the tooth. The receptacle may resemble a bulb that when compressed will expel its contents into the periodontal pocket, or defect. Upon installation of the first tray layer on the patient's teeth, the medication sits and does not leave the bulb or receptacle, allowing for the tray to position exactly where it needs to be to be effective. A second tray is then fabricated that fits over the first tray made out of a more rigid material that when positioned over the first tray pushes on the medicament bulb chamber, expelling the contents into the desired place. This tray syringe can be composed using more than two layers, such as a third layer that acts as a focusing layer or micro-needle or cannula. When positioned before or in front of the layer containing the medicament, it can guide the medicament into the periodontal pocket or defect. As the third tray engages the medicament tray, which is now the second tray, the medication is forced onto the surface of the teeth and subgingivally by the seal into any pockets in the patient's gums proximate the teeth. The first tray layer acts as the barrel of the syringe holding the medicament. The second tray layer, which fits over the first tray layer and is compressed against it acts as the plunger. The system can have a third layer that directs the medicament into a more focused delivery acting as the needle. Methods for fabricating the trays in the tray syringe system, loading the trays with medicaments, and delivering the medicaments into the periodontal pocket or defect are also described herein.

One object of the present invention is to provide an improved periodontal medicament delivery tray system, and method for treating periodontal disease by providing portal from outside the mouth into the periodontal pocket for introduction of either cleaning tools or cleaning liquids or medicaments. Thus, as noted above, in one embodiment, the present invention relates to a tray system composed of one or more layers of material that when combined and used in conjunction with each other work as periodontal aid which is fitted to one or more teeth of a patient's upper or lower dental arch provided for the application of medications to the teeth or gum tissue, bone or periodontal ligament for treatment of periodontal disease.

Another facet of the present invention is that the tray allows for the introduction of an interdental cleaning device and guides a cleaning object or medicament into the periodontal pockets, repeatable and in the exact location every time. The same tray can be attached to a liquid source that directs liquid streams into the periodontal pockets. The trays are constructed from a variety of resilient materials molded to conform to the teeth, gum tissues, and jaw bones, including at least one layer of material, but can include multiple layers, molded into trays that are compressible and returns to original shapes after deformation.

The first tray layer when formed has one or more holes drilled or fabricated directly above, or proximate to, one or more periodontal defect(s)/pocket(s) using a periodontal charting for positioning of the entries into the periodontal defects. Once the desired area, or areas, needing treatment are marked on a dental cast of the patient, a fitting is affixed to each hole in the tray using a glue, acrylic, or other means of mechanical friction or sandwiching the fitting between two layers of the tray. A connection from the fitting is then attached to a tube, hose, cannuli made from disposable rubber goods. These tubes can be connected to an additional fitting on the other side to allow for a polished edge and or an additional plumbing connection to be utilized.

If a doctor needs to treat multiple periodontal pockets resulting in multiple holes drilled, multiple fittings will be attached with multiple tubes. These tubes can be attached to a plastic or metal framework can be used to gang these tubes together in a row. This assembly can be attached to the tray or hand from the tray. The assembly housing multiple tubes can be numbered or marked identifying the areas using colors, or symbols aiding the end user in working with the appliance. Through each opening of the fitting connected to the tube connected to the fitting affixed to the tray, a liquid or micro brush, or pressurized liquid spray, or sonically energized liquid medicament stream can be pushed deeply into the periodontal pocket resulting in lavage or curettage. Such form of cleaning will not harm the tissues with in the periodontal pocket such as tooth cementum that is necessary for re-building of bone creating a new attachment to the tooth. The fittings attached to the tray that communicate with the oral cavity can be loaded like a gun with medicaments which can then be plunged through the tube into the periodontal defect, or through use of a propellant like air, or a jet stream from a compressed gas container. The tray system can be used with any medication used to treat periodontal disease or other disease of the mouth. Examples of such medicaments include, but are not limited to, antimicrobial agents, steroids, antifungal agent, sterilants, conditioners, fluorides, dentin desensitizers, antivirals, anesthetics, oxygenases, enzymes, peroxides, and therapeutic bacterial strains, any suitable combination of two or more thereof, or others.

The tray system of the present invention can be adjusted or re-fabricated according to the stage of periodontal disease suffered by the patient by creating more than one tray as the treatment progresses. Gingival tissues that are swollen may shrink and therefore the opening into the periodontal pocket may move from where the first tray is fabricated. When constructing the tray, the first layer of the tray system is constructed from a cast representative of the patient's teeth and surrounding gum tissue created from either a digital scan of the patient's mouth or any type of dental impression using any suitable dental impression material.

The tray system of the present invention can also be fabricated to hold in contact to the periodontal pocket one or more unit-dose medicament capsules that when crushed against the tooth/gum surface and the tray, releases medicaments into the areas to be treated.

Turning to a detailed discussion of the present invention, initially a detailed periodontal examination is performed on a patient by a licensed dentist, dental hygienist or periodontist. A periodontal charting is performed. Periodontal pockets that are deeper than 3 mm are highlighted and marked. Dental impressions are taken of the patient and stone casts are poured up in dental stone. The periodontal chart is then reviewed and the areas of the tooth/gingiva surfaces in which dental pockets deeper than clinical acceptance are marked on the stone casts using an ink pen. This marked cast is now used to fabricate the tray syringe on.

Another method for more accurately reproducing the periodontal pocket location and opening is also described. A detailed periodontal examination is performed on a patient by a licensed dentist, dental hygienist or periodontist. A periodontal charting is performed. Periodontal pockets that are deeper than 3 mm are highlighted and marked. Small, flexible barbed broaches or points are now inserted into the actual periodontal pockets in the mouth. These broaches or points either stay in place due to the depth of the pocket or defect, or are held in place the application of a curable composite resin. Dental impressions are taken of the patient and stone casts are poured up in dental stone. In all locations where a broach or point were placed, a hole in the cast will be present indicating not only the location of the periodontal disease, but a detailed access hole will be present allowing the tray syringe fabrication to be more accurate than conventional impression techniques with a transfer from a periodontal chart.

Fabrication of the first tray layer is the next step. Once the dental cast is fabricated with the access areas either marked on the cast or actually created in the stone using the broach-impression technique, a small shape is placed on the dental cast used a framework for the first layer of tray material.

A two layer bulb tray can now be fabricated by placing dental composite resin injected from a syringe in the shape of a ball or ovoid shape to create the framework for the soon to be created bulge or recess that will form in the first tray layer. Due to composite resins ability to stick to the dental model and harden after curing, it makes for excellent material to place on the stone cast. Another method to create the same effect is to take air gun BBs from a local hobby store, and glue them to the cast using superglue. Salt or sugar or other water soluble formulations that can go from the solid state and easily dissolve in water can be formed in a desired shape and used in place of the composite resin or BB. Once all the BBs, or composite resin balls, are attached to the dental cast of the patient's mouth vacuum-formed heated EVA material heat suck-down is made over the cast with the projections. This now becomes the first tray layer. It should be noted that although the first tray layer is disclosed to be formed from EVA the present invention is not limited thereto. Rather, any other suitable flexible and/or resilient polymer or plastic compound can be utilized so long as such a compound is able to be placed in an individual's mouth.

The first tray layer is now removed from the cast and any excess material is removed. The first tray layer is now placed back on the model and an impression is taken of it using alginate impression material. After the impression of the first tray layer on the cast is taken, it is poured up dental stone. A knife is now used, or a spinning cutting bur on a dental motor is used, to abrade or divot or dent or remove the budges or positives in the stone cast which represent the recesses or bulbs of the first tray layer. This stone cast is now placed in the dental vacuum form machine and a second layer of a harder plastic material is vacuum-formed over the cast. When this layer is removed from the cast, trimmed and placed over the first tray layer it becomes a second tray layer of the present invention. The second tray layer is designed to depress the recesses in the flexible EVA material and expel their contents. The medicament of choice is now syringed into the first tray layer's bulge or recess using a standard medical syringe having a needle. The first syringe layer is loaded with medicament and is placed into the mouth firmly seating it over the teeth and gingival. The fit should be firm and stable. Now the second tray layer which is designed to be the harder tray layer is placed over the first layer and pushed up back and forth by the patient's hands. The motion can be one swift motion, or a pumping motion. Once the medicament is delivered, the tray syringe can be removed and cleaned for the next application.

A three layer bulb tray can also be fabricated with a slight modification. Prior to placing the resin or BB on the cast to create a bulge for the medicament, a layer of EVA is first thermoformed over the cast. Then holes are drilled to communicate to the periodontal pockets. Then the BBs or composite resin are placed in the holes drilled through the EVA layer. A second layer of EVA is then thermoformed over the first layer, sandwiching the BBs or composite resin between the two layers. The two fused layers are then removed and the BBs or composite resin balls are pushed through the holes, leaving a recess or bulb to accept the medicament. The steps are the same in then fabricating the hard plunger layer as the two layer bulb tray discussed above.

A two layer capsule tray can be fabricated by substituting the BBs or composite resin with a hard replica of a micro unit-dose medicament capsule. Following the same fabrication instruction as the two layer bulb tray, the hard replica creates the cavity for the unit-dose capsules to load into.

A one layer Lavage tray is also within the scope of the present invention. In one embodiment, a hard thermoformed plastic material is formed over the dental cast that is marked showing the periodontal pockets. Holes are drilled through the hard plastic in order to communicate with the pockets openings on the cast. Couplings are fitted and affixed to the hard tray layer that will accept cannulai. An irrigation source is attached to the cannulai and provides site specific directed irrigation. These cannulai can be ganged together as to allow the user easy attachment to the irrigant liquid or can be daisy chained or ran in parallel to allow the irrigant to reach multiple pockets at the same time.

A one layer curettage tray is also within the scope of the present invention. In one embodiment, a hard thermoformed plastic material is formed over the dental cast that is marked showing the periodontal pockets. Holes are drilled through the hard plastic in order to communicate with the pockets openings on the cast. Couplings are fitted and affixed to the hard tray layer that will accept cannulai. Micro-instruments attached to fishing line can then be thread through the cannulai reaching the periodontal pockets in the mouth. These cannulai can be ganged together as to allow the user easy access to multiple pockets by simply moving the micro instruments through the ganged cannulai. This tray can be also used to push medicaments deep into the periodontal pockets by loading medicaments into the end of the coupling touching the periodontal pocket opening and using a plunger attached to the fishing line filament to push the meds deep into long 4 to 10 mm pockets.

Due in part to the method by which the present invention is fabricated, a periodontal tray is produced that permits one to guide a cleaning object, or medicament, into one or more periodontal pockets in a repeatable and exact manner as desired by a doctor, or other treatment professional.

In another embodiment, the interdental tray system of the present invention includes at least one layer of resilient material, but can include multiple layers of resilient material, molded into trays that are compressible and return to their original shapes after deformation. Trays can be fused together, or can fit together and can be separated.

In another embodiment, the one or more pockets formed in the flexible first tray layer of the present invention can be individually, or collectively, replaced, or supplemented, by one or more holes, or openings, that are designed to communicate with one or more periodontal defect(s) or pocket(s). This permits the periodontal tray system of the present invention to function in conjunction with one or more syringes that can be used to inject one or more medicaments into a periodontal pocket.

Figure 2:
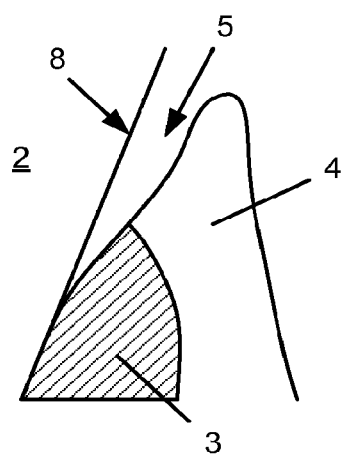
FIG. 2 is a close-up illustration of the root of a portion of a tooth and the surrounding bone structure.
Figure 3:
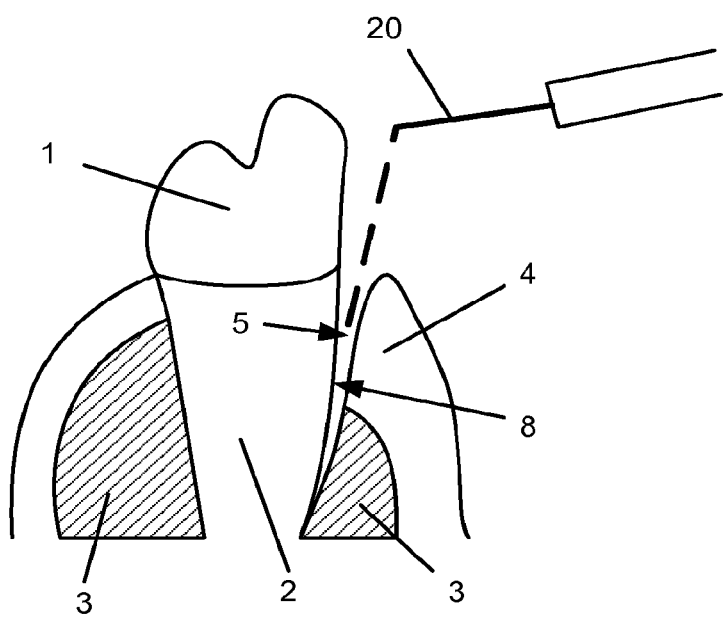
FIG. 3 is a close-up illustration of a portion of a tooth and gum area that suffers from periodontal disease showing a probe therein that is utilized to determine the extent of the periodontal disease.
Figure 4:
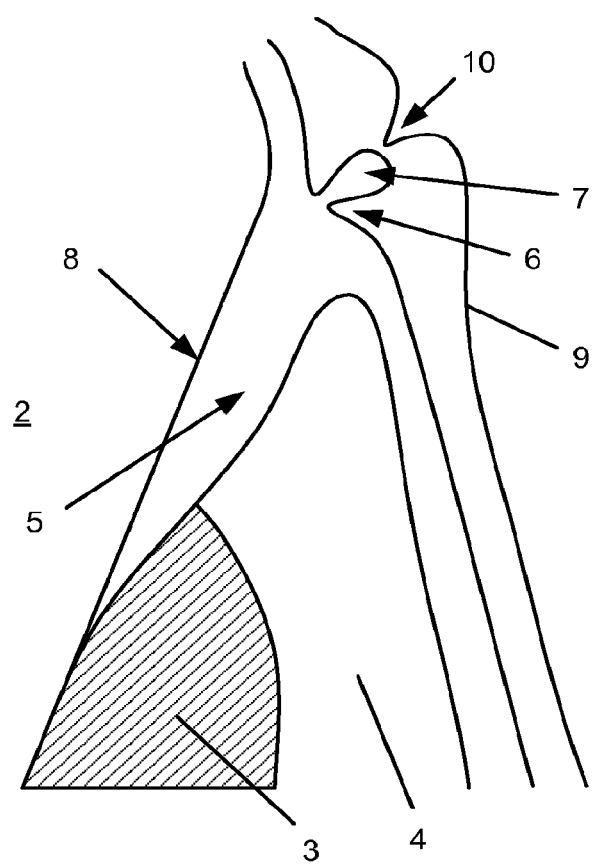
FIG. 4 is a close-up illustration of a portion of a tooth and gum area that suffers from periodontal disease showing a device designed to treat and/or manage periodontal disease, wherein the device is formed in accordance with one embodiment of the present invention.

Turning to the Figures, FIG. 1 is an illustration of a tooth 1 having a root 2 secured by surrounding bone 3 and gum 4. As can be seen in FIG. 1, a periodontal pocket 5 exists one side of the tooth 1 that exposes a portion of the root surface 8 of tooth 1. FIG. 2 is a close-up illustration of the tooth root 2, the surrounding bone 3, diseased area of the gum 4, and the exposed root surface 8. The periodontal pocket is represented by reference numeral 5. FIG. 3 is a close-up illustration of a tooth with a root 2 with a periodontal pocket 5 being measured with a periodontal probe 20. In system of FIG. 4, first tray layer 6 is formed from the resilient material, as is discussed above, and contains therein one or more pockets, indentations, or cavities 7 that correspond in location to periodontal pocket 5. The one or more pockets, indentations, or cavities 7 can be filled with one or more medicaments or compounds as disclosed above. Filling can be accomplished by any suitable manner including, but not limited to, a syringe. As is discussed above the periodontal tray system of the present invention, as represented in part by FIG. 4, also comprises a second tray layer 9 that may, or may not, contain one or more internal protrusions 10 designed to operatively engage a respective and/or corresponding pocket, indentation, or cavity 7. In the instance where second tray layer 9 comprises one or more internal protrusions 10 (see FIG. 4), the one or more internal protrusions 10 are designed to provide additional impetus for the release of the one or more medicaments contained in a respective and/or corresponding pocket, indentation, or cavity 7. However, the one or more internal protrusions 10 are not required in all embodiments of the present invention. In another embodiment, such protrusions 10 may be absent where the patient, or some other individual, provides the necessary pressure to cause the ejection of the medicament contained in the one or more pockets, indentations, or cavities 7 to be ejected. In one embodiment, the one or more compounds, or medicaments, contained in the one or more pockets, indentations, or cavities 7 of the first tray layer of the present invention can be in a gel form so as to stay put until dispensing thereof is desired. In another embodiment, the one or more compounds, or medicaments, contained in the one or more pockets, indentations, or cavities 7 of the first tray layer of the present invention can be in a liquid form where the one or more pockets, indentations, or cavities 7 are designed to have a slightly smaller opening at the internal surface so as to take advantage of a liquid surface tension property.

Figure 5:
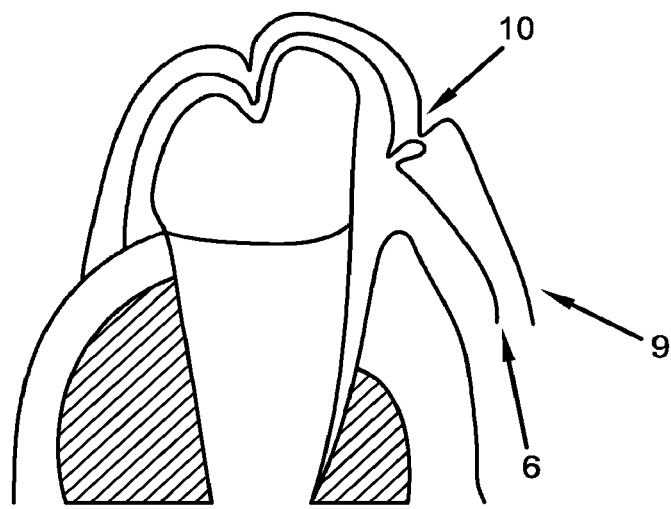
FIG. 5 is a cross-sectional illustration of a tooth and surrounding gum area that suffers from periodontal disease showing a device designed to treat and/or manage periodontal disease, wherein the device is formed in accordance with one embodiment of the present invention.
Figure 6:
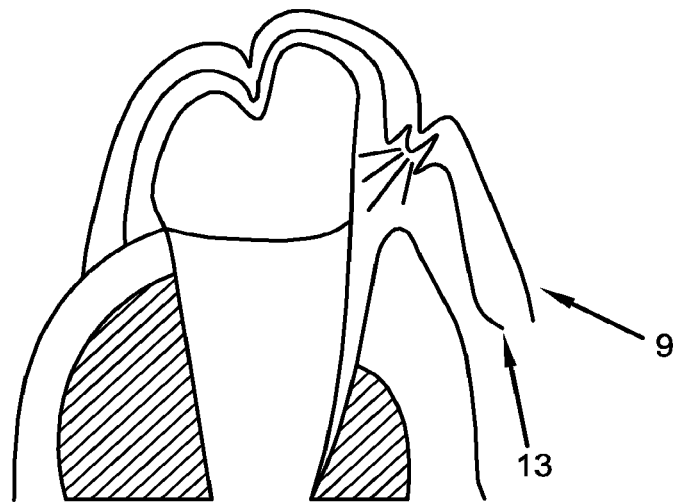
FIG. 6 is a cross-sectional illustration of the device of FIG. 5, where the device has been deployed.

Turning to FIGS. 5 and 6, FIGS. 5 and 6 illustrate a complete cross-sectional view of one tooth with a periodontal tray system of the present invention located there over. In FIG. 6, layer 13 corresponds to first tray layer 6 expect for the fact that pocket, indentation, or cavity 7 has been compressed by second tray layer 9. As would be apparent to those of skill in the art, a wide variety of sizes and shapes of the periodontal tray system of the present invention can be produced. As such, the present invention is not limited to complete mouth (upper and/or lower) trays. Instead, any shape of a partial tray or complete tray can be accomplished using the information disclosed herein. Protrusion 10 acts to engage pocket, indentation, or cavity 7 so as to accomplish the release of the one or more medicaments, or compounds, contained therein.

Figure 7A:
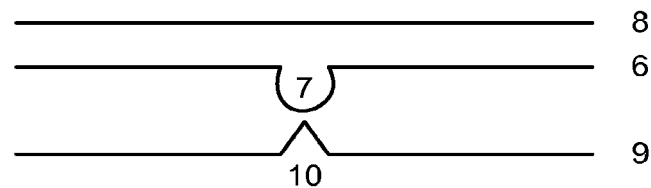
FIGS. 7A through 7C are illustrations of multiple layers of tray materials as they exist in various configurations.
Figure 7B:
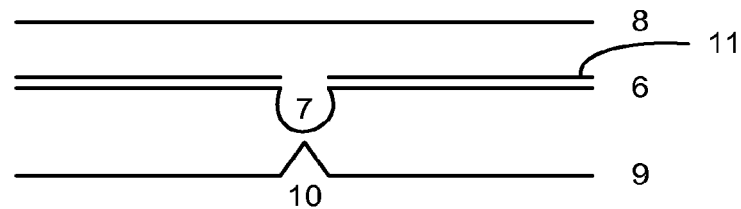
Figure 7C:
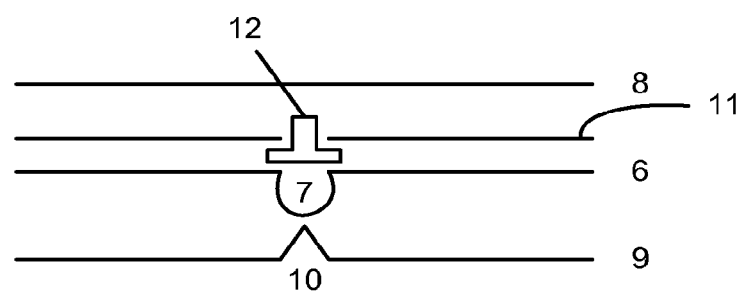

Turning to FIGS. 7A through 7C, these Figures are illustrations showing multiple configurations of tray materials. The tooth/gum surface is labeled 8. The hard, or second tray layer 9 with one or more protrusions and/or indentations 10 located therein are situated in such a position so that protrusion and/or indentation 10 pushes on the softer, or first, tray layer 6 thereby releasing medicament either directly as shown in FIG. 7A, or through an intervening layer 11 that is located between layer 6 and the surface of the tooth/gum 8 (see FIG. 7B). FIG. 7C illustrates an embodiment where a focusing needle 12 is located between layers 6 and 11.

Figure 8A:
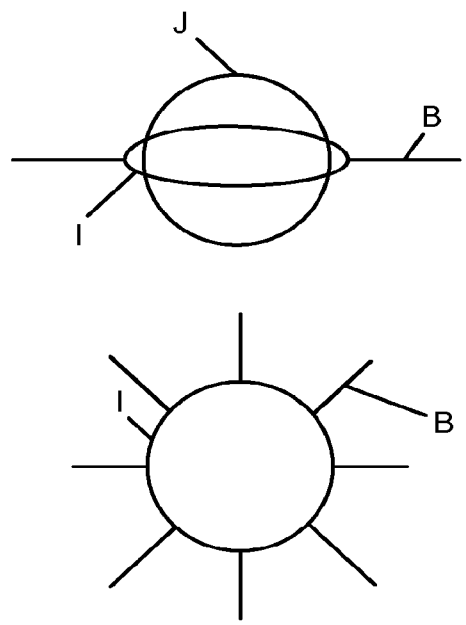
FIGS. 8A through 8B are illustrations of various layers of tray materials with a capsule medicament ring that is used to hold medicament capsules.
Figure 8B:
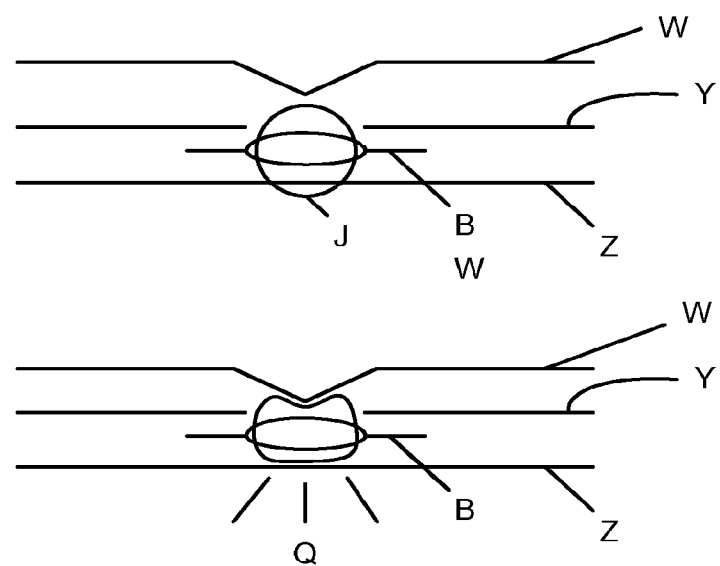

Turning to FIGS. 8A and 8B, FIG. 8A illustrates a medicament capsule holder I having flanges B and a medicament portion J, whereas FIG. 8B illustrates the medicament capsule holder sandwiched between two tray layers Y and Z. The medicament capsule holder I is secured, or maintained, in place by flanges B formed therein. The hard, or second, tray layer W crushes the capsule I thereby releasing medicament Q when layer W is pushed up against the medicament portion J.

Figure 9A:
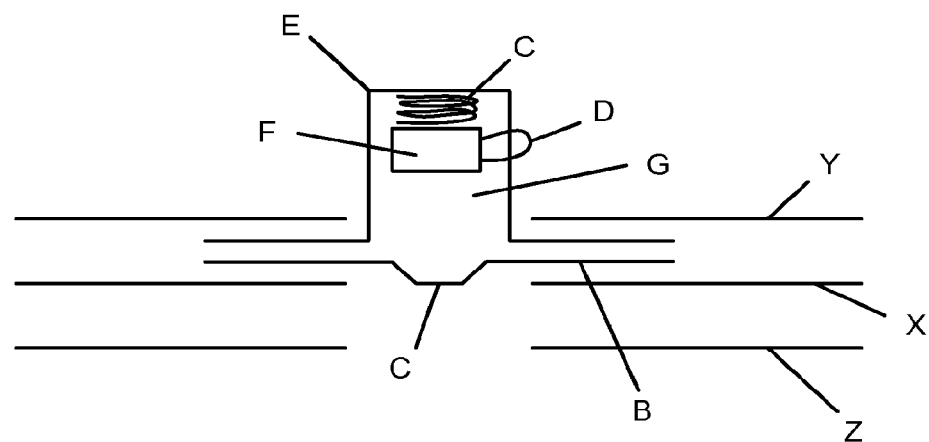
FIGS. 9A and 9B are illustrations of a micro-spring loaded syringe that attaches to a tray layer.
Figure 9B:
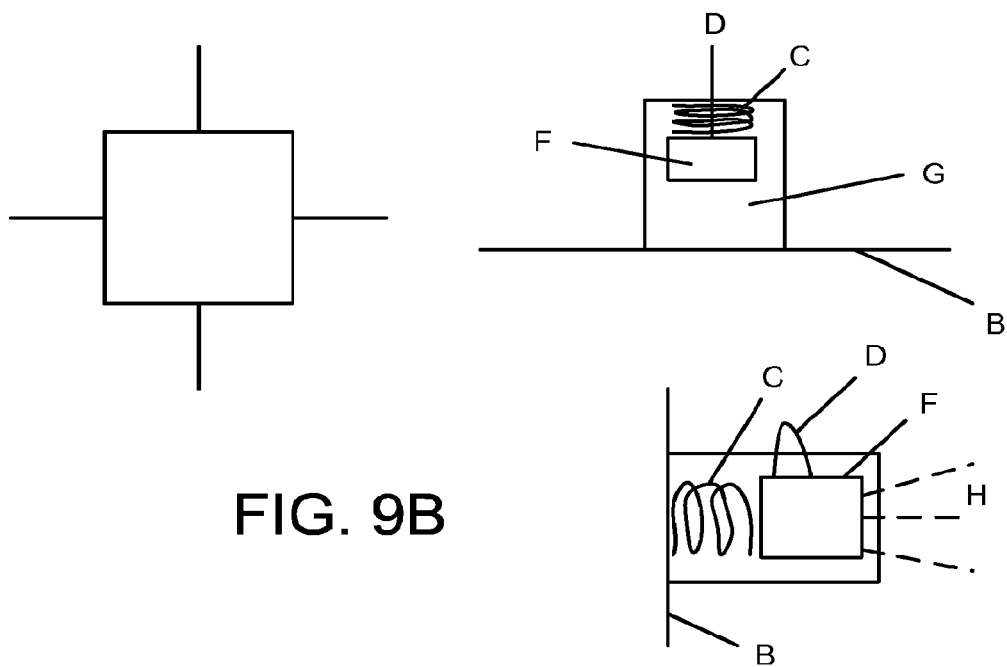

FIGS. 9A and 9B illustrate a mechanical micro-syringe that attaches to the tray layers of a two layer system described above. As a barrel F is compressed against a spring C, latch D engages the side of the syringe E and energizes. When a hard tray or instrument comes in contact with lever D, the spring pushes the barrel F down and releases the medicament H.

Figure 10:
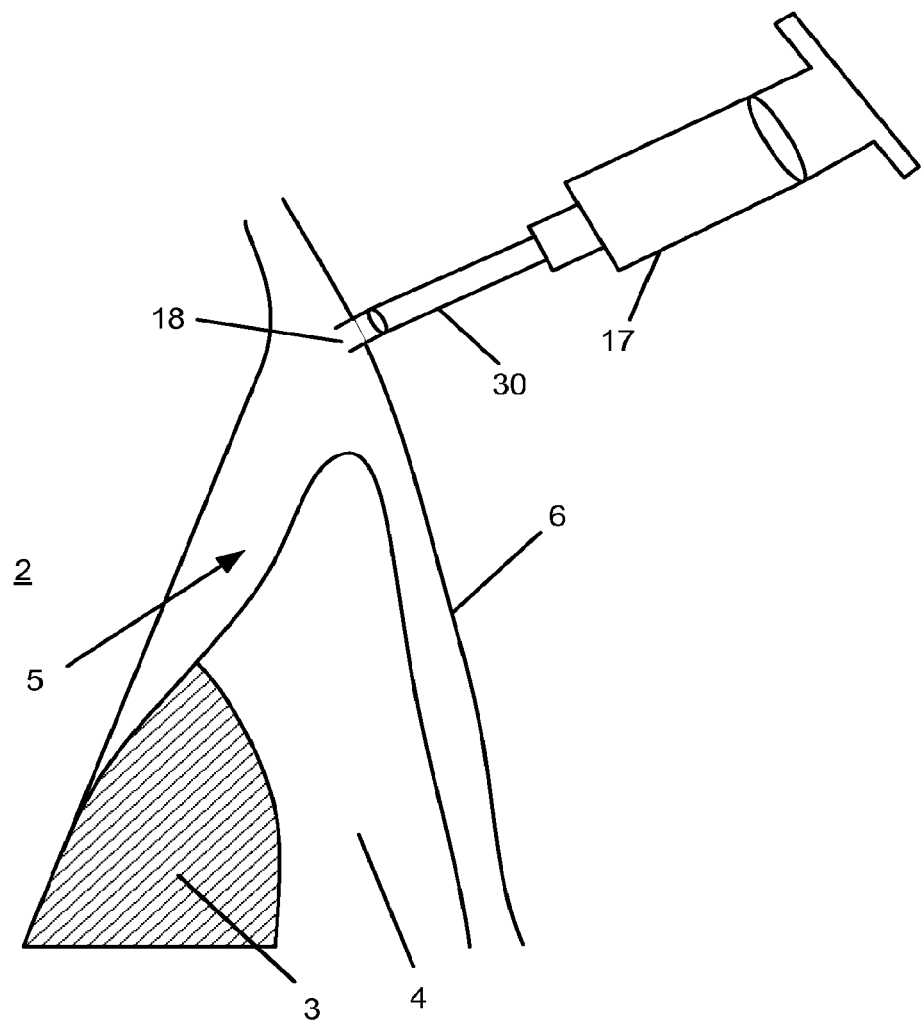
FIG. 10 is an illustration of one embodiment of a periodontal tray of the present invention that contains one or more openings that are designed to engage one or more syringes.

Turning to FIG. 10, FIG. 10 illustrates a periodontal tray system of the present invention that contains only a first resilient layer 6 as described above. In this embodiment, tray layer 6 contains one or more holes, or openings in which a coupling or fitting is attached 18 that can be operatively engaged with one or more cannulai 30 that attaches to one or more syringes 17. As would be apparent to those of skill in the art, multiple opening, or holes, 18 could be operatively coupled, or engaged, to one syringe 17 through a series of multiple tubes or cannulai 30 connected to the end of a syringe. In another embodiment, syringe 17 can be replaced by a syringe, or a squeeze bottle or container that is designed to be decupled from the supply line that is in connection with the one or more holes, or openings, 18 in first tray 6.

As would be apparent to one of skill in the art, opening 18 and cannulai 30 can also be used to place, supply, or insert various types of micro-instruments into one or more periodontal pockets 5. Thus, given the device that one desires to insert through cannulai 30, cannulai 30 can be appropriately designed to accommodate such devices.

Figure 11:
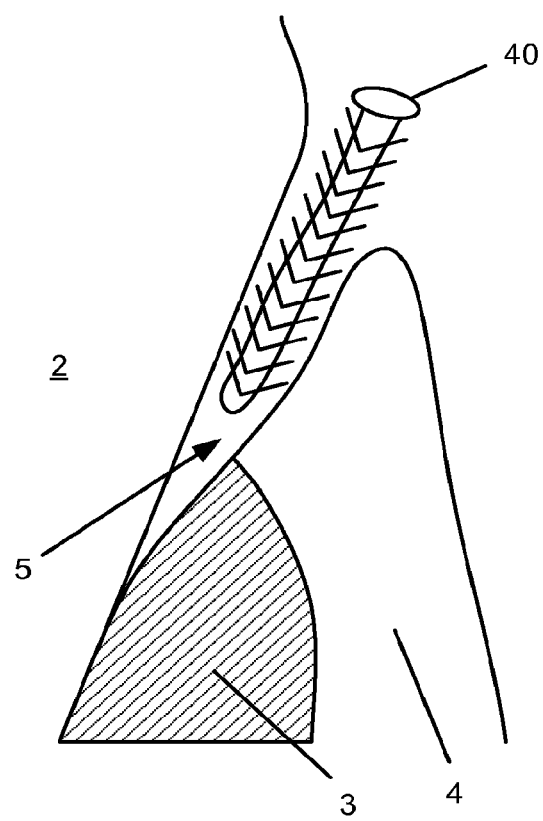
FIG. 11 is an illustration of a barbed broach placed in the periodontal pocket defect.
Figure 12:
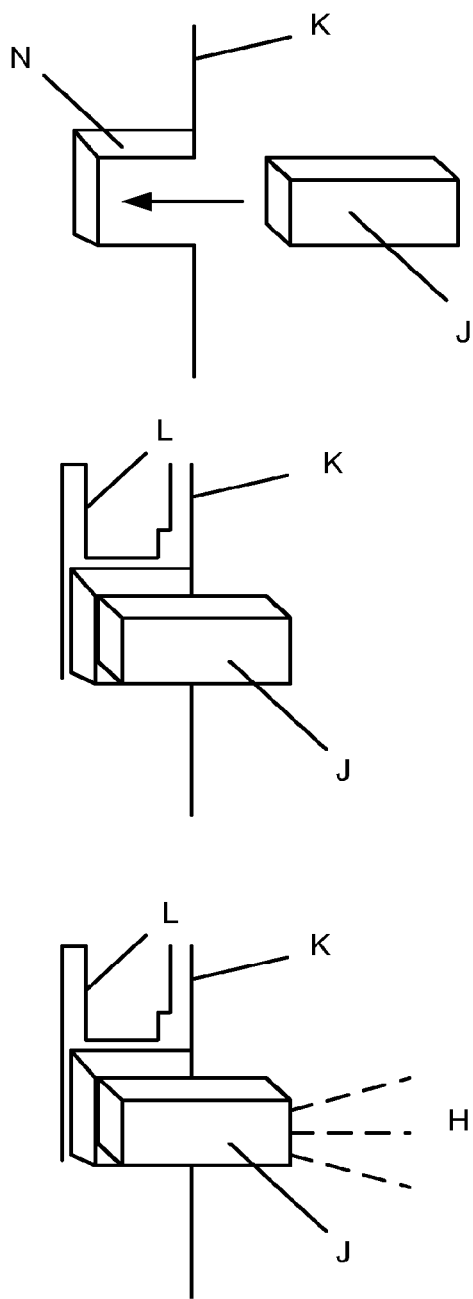
FIG. 12 is an illustration of two tray layers, one that receives a medicament capsule and holds it intimate to the gum/tooth surface and a second layer that crushes it and expels its contents.
Figure 13A:
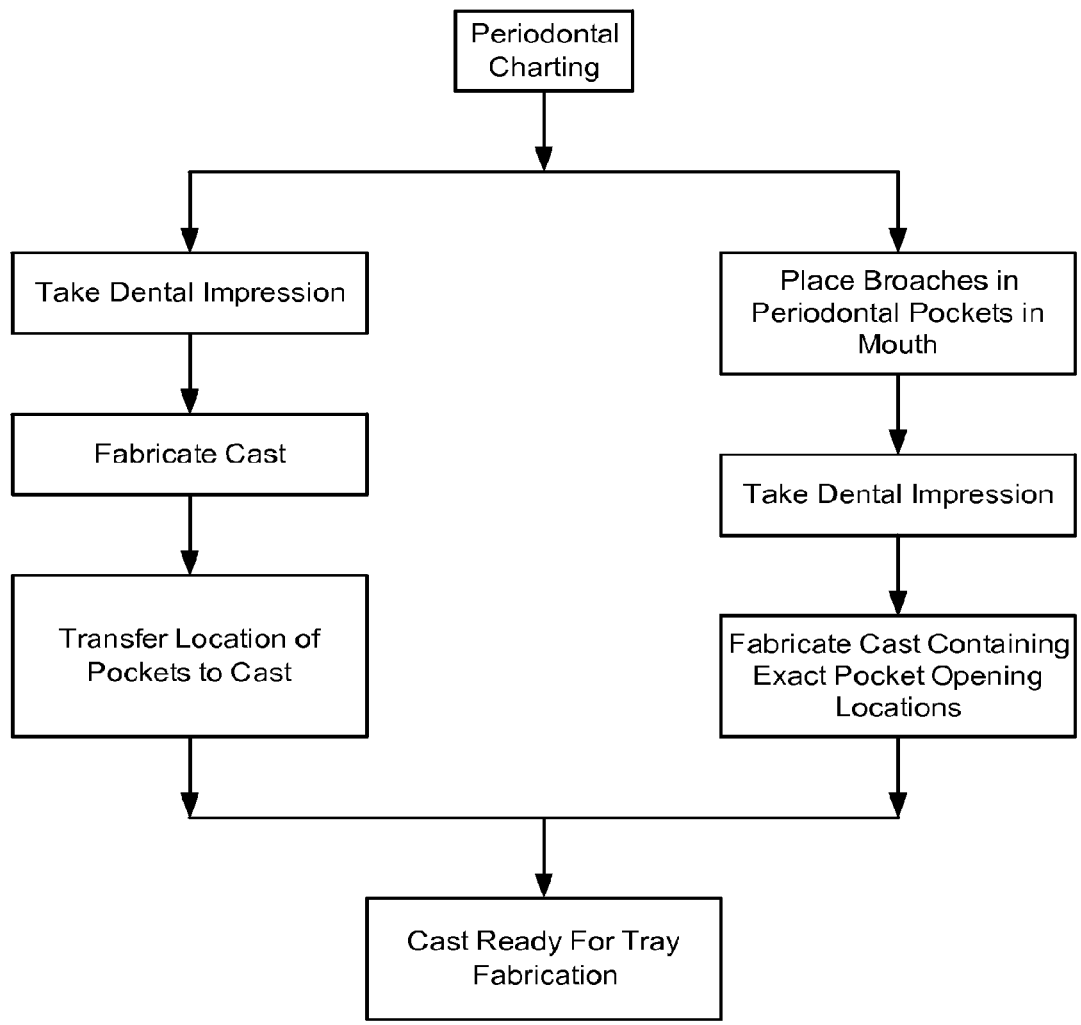
FIGS. 13A through 13F are flow charts representing various methods that fall within the scope of the present invention.
Figure 13B:
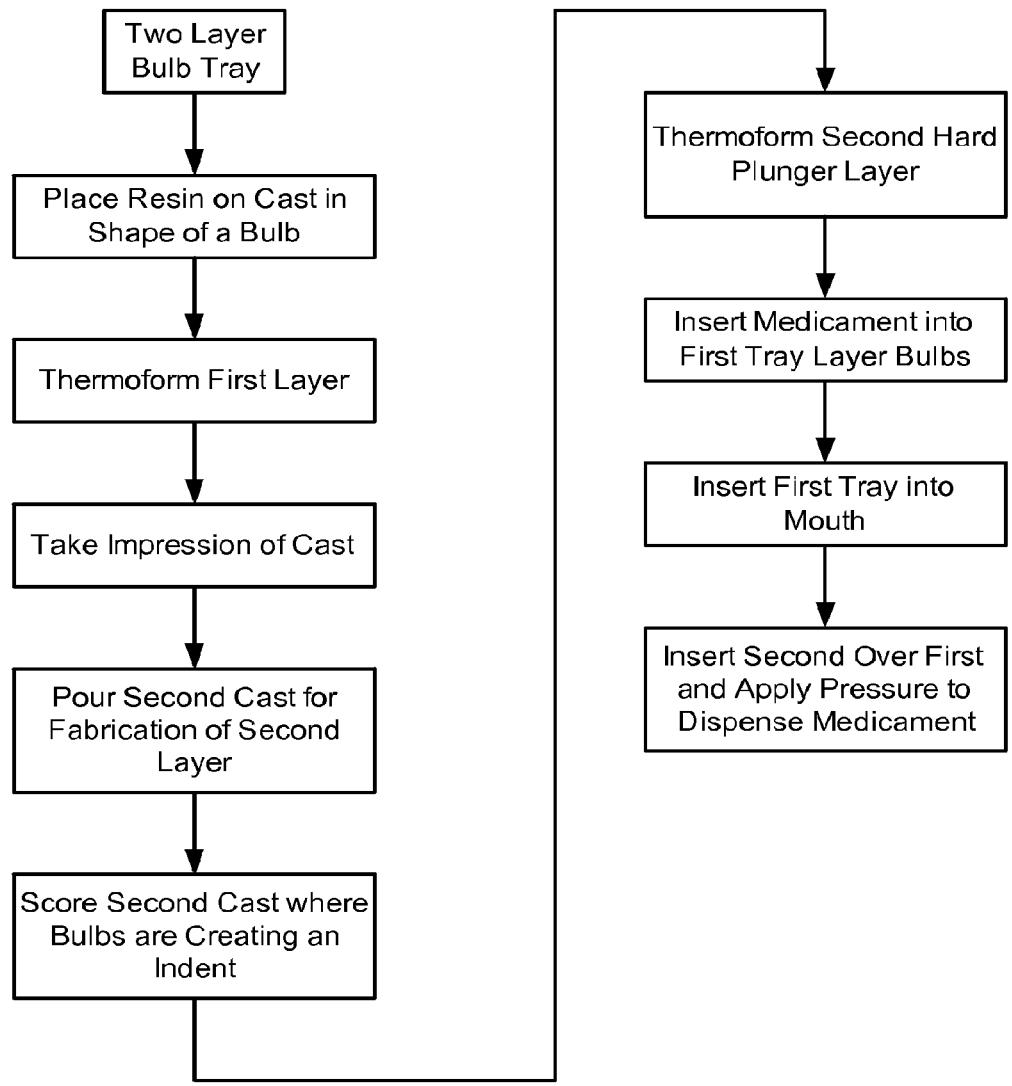
Figure 13C:
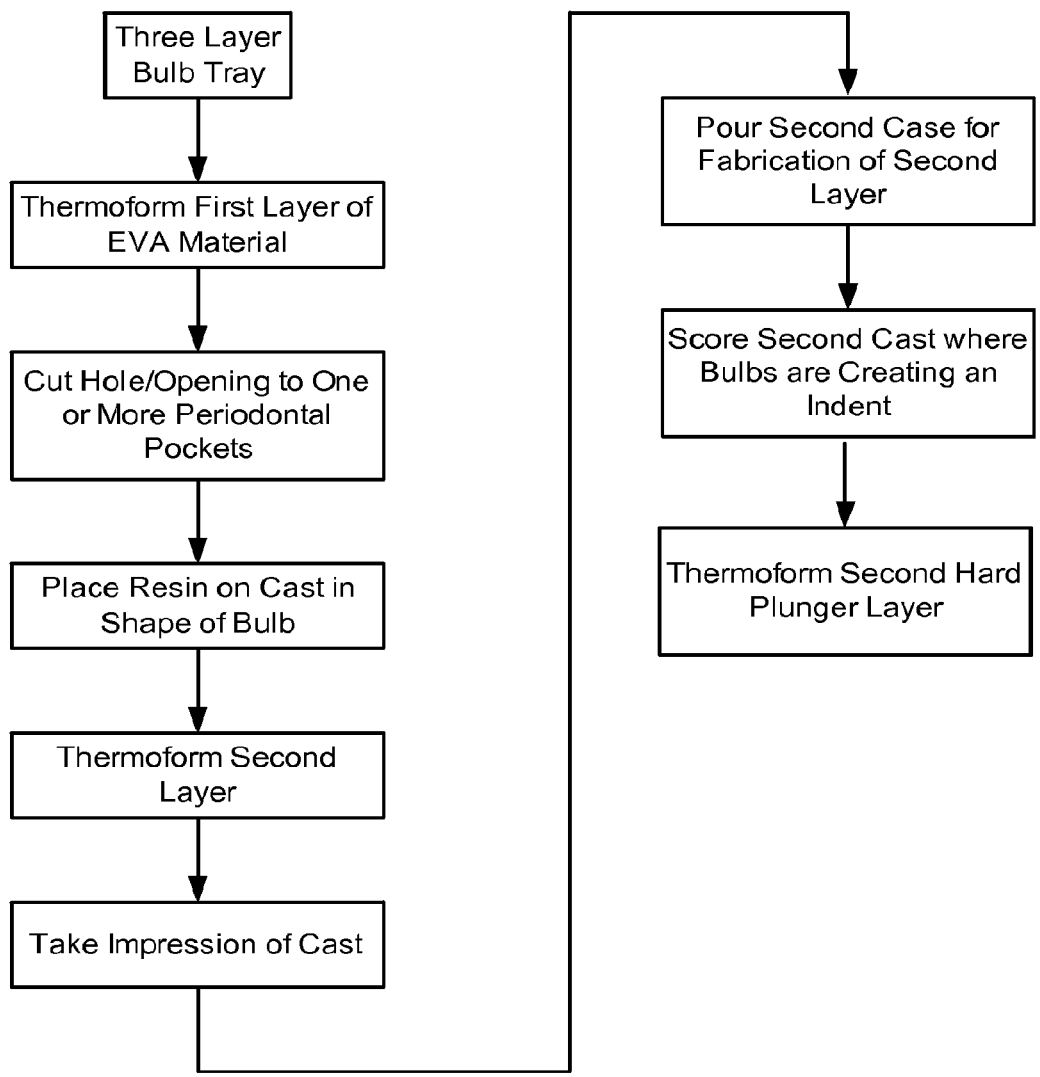
Figure 13D:
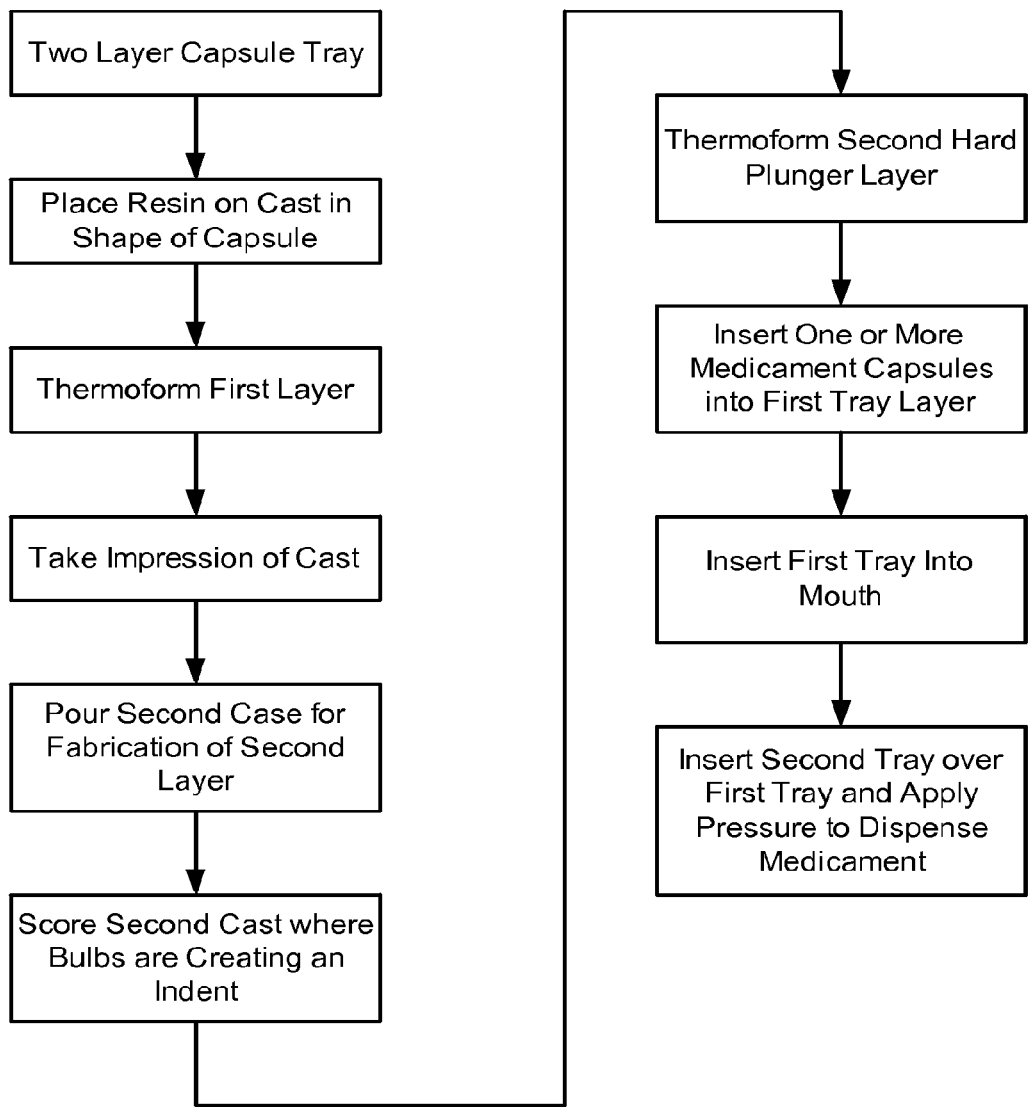
Figure 13E:
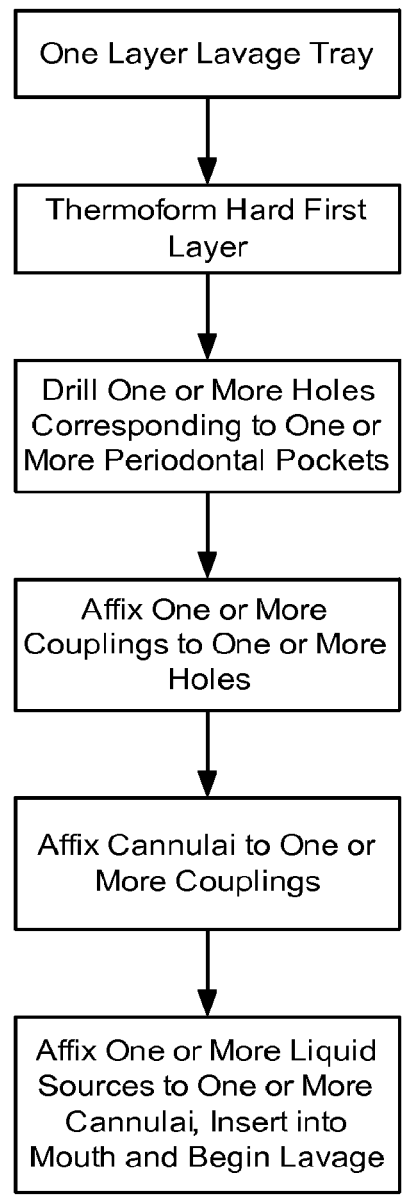
Figure 13F:
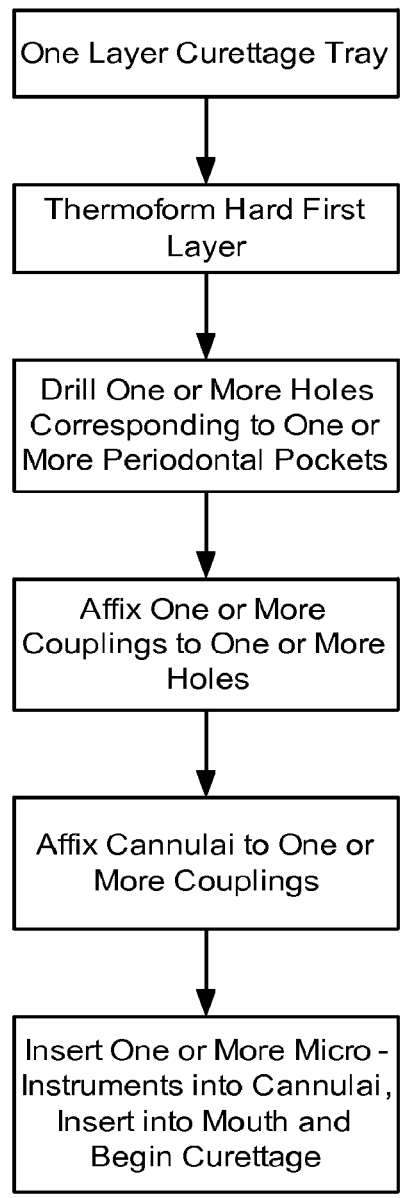

FIG. 11 is an illustration of a barbed broach, or point, 40 placed into a periodontal defect, or pocket, 5. The tooth is 2, the bone holding the tooth in 3, and the gum tissue 4. FIG. 12 illustrates a tray layer K. which is designed to accept a medicament capsule J. Cut-out N. accepts a hard tray layer L. and crushes the medicament layer. FIGS. 13A through 13F are flow charts detailing multiple methods of the present invention.

In one embodiment, the invention described here allows for repeatable delivery of medicaments into a periodontal pocket through the creation of a true syringe when using the invention with a plunger pushed through a tube into the periodontal pocket. In another embodiment, the present invention also permits for repeatable curettage using fine instruments pushed through the tubes into the periodontal pocket. In still another embodiment, the present invention permits for the repeatable lavage, by using the tube to connect a source of medicated or non-medicated liquids energized, or not, directed into the periodontal pocket.

In another embodiment, the present invention relates to a periodontal tray system comprising: a first inner tray layer that is designed to conform to at least a portion of an individual's mouth, wherein the first inner tray layer is designed to have one or more indentations, or pockets, formed therein that correspond to at least one area of periodontal disease; and a second outer tray layer that is designed to operatively engage the first inner tray layer, wherein the have one or more indentations, or pockets, formed in the first inner tray layer contain one or more medicaments, or compounds, designed to treat one or more aspects of periodontal disease, and wherein the second outer tray layer is designed to operatively engage the first inner tray layer so as to permit the delivery of the one or more medicaments, or compounds, contained in the one or more indentations, or pockets, formed in the first inner tray layer into the at least one area of periodontal disease.

In still another embodiment, the present invention relates to a periodontal tray system comprising: a first tray layer that is designed to conform to at least a portion of an individual's mouth, wherein the first inner tray layer is designed to have one or more openings therein that correspond to at least one area of periodontal disease, wherein the one or more openings formed in the first tray layer are designed to operatively couple one or more syringes, or micro-syringes, and wherein the one or more syringes, or micro-syringes, contain one or more medicaments, or compounds, designed to treat one or more aspects of periodontal disease.

In still another embodiment, the present invention relates to a periodontal tray system comprising: a first tray layer that is designed to conform to at least a portion of an individual's mouth, wherein the first inner tray layer is designed to have one or more openings therein that correspond to at least one area of periodontal disease, wherein one or more openings formed in the first tray layer are designed to operatively couple with unit-dose medicament capsules, and wherein the one or more capsules contain one or more medicaments, or compounds, designed to treat one or more aspects of periodontal disease. In one embodiment, the capsules are then activated, crushed, punctured, or exploded with the application of either a second tray or other hand-held device that releases the medicament into the mouth.

In still another embodiment, the present invention relates to a method to fabricate the periodontal tray system, the method comprising the steps of: (i) placing one or more small barbed broaches into one or more periodontal pockets, wherein the one or more small barbed broaches are designed to function in conjunction with a dental molding material, or impression material, that is used to duplicate various teeth and mouth structures; (ii) creating a mold of one or more areas surrounding the one or more periodontal pockets, wherein the mold contains one or more openings formed therein that correspond to the placement of the one or more small barbed broaches; and (iii) using the mold of Step (ii) as either a periodontal tray, or as an impression to produce a periodontal tray, wherein the periodontal tray contains one or more openings therein that correspond to one or more periodontal pockets, wherein the one or more openings are designed to connect to one or more treatment devices (e.g., a tube/syringe combination, or a syringe).

Regarding the micro-syringes discloses herein, such syringes have been reduced in size to work with one or more tray systems which, in one embodiment, permit the placement, or location, of one or more of these micro-syringes in the mouth of a patient in a desired area where, for example, periodontal issues exist. Activation of such syringes can be done with a second tray, or with other devices, such as timed triggers, hand held instruments that engage the micro-syringe and allow the release of the plunger.

In another embodiment, the present invention relates to a micro-syringe that attaches to a tray that delivers medicaments into the mouth where the construction of the micro-syringe involves a micro spring loaded medicament syringe that attaches to the one or more layers of a tray in accordance with the present invention, and wherein loading is possible through the compressing of a spring that holds a plunger back until the plunger is deployed by pressing a latch. As would be apparent to those of skill in the art, multiple micro-springs can be attached to a tray to provide multiple sites therapeutic treatment Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A periodontal tray system comprising:
  a first inner tray layer that is designed to conform to at least a portion of an individual's mouth, wherein the first inner tray layer comprises one or more indentations or pockets formed therein; and
  a second outer tray layer that is designed to operatively engage the first inner tray layer, wherein the one or more indentations or pockets formed in the first inner tray layer contain one or more medicaments or compounds designed to treat periodontal disease,
  wherein an inner surface of the second outer tray layer contains one or more raised areas or protrusions that are designed to respectively engage the one or more indentations or pockets located in the first inner tray layer, and wherein the second outer tray layer is designed to operatively engage the first inner tray layer, where the one or more raised areas or protrusions of the second outer tray layer operatively engage the one or more indentations or pockets of the first inner tray layer, so as to permit delivery of the one or more medicaments or compounds from the one or more indentations or pockets formed in the first inner tray layer into the at least one area of periodontal disease in the individual's mouth.

2. The periodontal tray system of claim 1, wherein the first inner tray layer is formed from a resilient and/or flexible polymer, plastic compound, an acrylic, synthetic or natural rubber, or a compound that is moldable or formable using chemical curing or heat-based vacuum forming.

3. The periodontal tray system of claim 2, wherein the first inner tray layer is formed from ethylene-vinyl acetate (EVA).

4. The periodontal tray system of claim 1, wherein the first inner tray layer is formed from two layers of ethylene-vinyl acetate (EVA) that are fused together forming the indentations, or pockets.

5. The periodontal tray system of claim 1, wherein the one or more indentations or pockets formed in the first inner tray layer contain one or more antimicrobial agents, one or more steroids, one or more antifungal agents, one or more sterilants, one or more conditioners, one or more fluorides, one or more dentin desensitizers, one or more antivirals, one or more anesthetics, one or more oxygenases, one or more enzymes, one or more peroxides, one or more therapeutic bacterial strains, or a combination of two or more thereof.

6. The periodontal tray system of claim 1, wherein the indentations or pockets formed in the first inner tray layer are reloadable multiple times with the one or more medicaments or compounds from a syringe, a container or a unit-dose capsule that contain the one or more medicaments or compounds.

7. The periodontal tray system of claim 1, wherein the indentations or pockets formed in the first inner tray layer are reloadable multiple times with the one or more medicaments or compounds from one or more unit-dose capsules that when crushed, melted, or dissolved release the one or more medicaments or compounds.

8. The periodontal tray system of claim 1, wherein the second outer tray layer is formed from a rigid polymer, plastic compound, a rigid acrylic compound, a heat moldable and/or vacuum formable material, or synthetic or natural rubber.

* * * * *